(12) United States Patent
Xiao

(10) Patent No.: US 7,115,124 B1
(45) Date of Patent: Oct. 3, 2006

(54) DEVICE AND METHOD FOR TISSUE ABLATION USING BIPOLAR RADIO-FREQUENCY CURRENT

(76) Inventor: Jia Hua Xiao, 1574 Rockford Rd., Apt 319, Plymouth, MN (US) 55446

( * ) Notice: Subject to any disclaimer, the term of this patent is extended or adjusted under 35 U.S.C. 154(b) by 101 days.

(21) Appl. No.: 10/973,056

(22) Filed: Oct. 25, 2004

Related U.S. Application Data

(60) Provisional application No. 60/519,183, filed on Nov. 12, 2003.

(51) Int. Cl.
*A61B 18/14* (2006.01)

(52) U.S. Cl. ...................................................... 606/41

(58) Field of Classification Search ................ 606/41, 606/45–52
See application file for complete search history.

(56) References Cited

U.S. PATENT DOCUMENTS

| | | | |
|---|---|---|---|
| 5,693,078 A | 12/1997 | Desai et al. | |
| 5,868,740 A | 2/1999 | LeVeen et al. | |
| 6,514,252 B1 | 2/2003 | Nezhat et al. | |
| 2002/0111615 A1* | 8/2002 | Cosman et al. | 606/41 |
| 2002/0120261 A1* | 8/2002 | Morris et al. | 606/41 |

\* cited by examiner

*Primary Examiner*—Lee S. Cohen
(74) *Attorney, Agent, or Firm*—AZ Patent Law Firm

(57) ABSTRACT

A device for tissue ablation comprises plural arrays of segmented needle electrodes, each of which contains a plurality of electrically conductive segments, a plurality of non-conductive joints, and a needle tip. Each of the electrically conductive segments is wired to a radio-frequency electrical power source and can be connected to and disconnected from the power source. After the needle electrodes of the device are penetrated into a target tissue to be ablated, the intended volume of ablation can be configured in three dimensions. Thus, the device allows physicians to effectively control ablation boundaries.

25 Claims, 5 Drawing Sheets

DEVICE AND METHOD FOR TISSUE ABLATION USING BIPOLAR RADIO-FREQUENCY CURRENT

CROSS-REFERENCE TO RELATED APPLICATION

This patent application claims the priority from the provisional application 60/519,183 accorded with a filing date of Nov. 12, 2003.

FIELD OF INVENTION

This invention relates to medical devices and, in particular, to multi-needle-electrode array and the technology of employing bipolar radio-frequency energy for ablation of diseased tissues such as tumors, cancerous tissues, and abnormal tissues in living subjects.

BACKGROUND OF THE INVENTION

In treatment of tumors and cancerous tissues in human body, various methods are available, which include medication, radiation, dissection and ablation. Radio frequency (RF) ablation is commonly used to treat diseased tissues. RF ablation is a tissue treatment by which two or more electrodes are inserted into the vicinity of a diseased tissue and an alternating electrical current, typically at a frequency of a few hundred kHz, is applied to the tissue through the electrodes to ablate the tissue between the two electrodes. It is commonly believed that when the RF current passes through the tissue, electrical energy transforms into heat by what is known as Joule heating effect, and when the temperature of the tissue is high enough (it is generally believed that the temperature needs to be above 55° C.), the cells of the tissue between the two electrodes are destroyed. For most tissue ablation cases, it is desirable to ablate the tissues only within intended boundaries (e.g., desirable size and shape). Therefore, it is critical that the RF energy is directed only to the targeted tissue within the desirable boundaries to minimize damage to the healthy tissues surrounding the targeted tissue.

"Le Veen Needle Electrodes", described by U.S. Pat. No. 5,868,740, is a device currently available on the market for the treatment of tumors and cancerous tissues. This device contains an array of deployable needles, which can be inserted into the tumor tissue, and a large grounding pad, which may be in contact with a large area of the skin of a patient. In an ablation operation, the needles are inserted into the diseased tissue and the ground pad is properly placed in contact with a large area of the skin of the patient. Then, an RF current is applied to all the needle electrodes at once. The current passes through the diseased tissue (and some normal tissues) at higher current density, the large area of skin at lower current density, and the grounding pad, going back to the RF power source. This technique is referred to as monopolar RF ablation technology. The drawback of the technique is that because the RF current goes through part of the healthy tissues, it sometimes causes unintended damages to them if the current is not carefully controlled.

In U.S. Pat. No. 5,693,078, Jawahar Desai discloses a device and technique for generating a large lesion to treat endocardiac tissue for ventricular tachycardia and other cardiac dysrhythmias. Desai used an array of electrodes, which was placed on the surface of the ablation zone and an RF power source that had a plurality of voltage outputs, each having an individual phase. Each individual electrode was connected to one of the individually phased outputs of the RF power source. When power was turned on, the electrode array together with the multi-phased RF power source produced plural current paths on the surface of the ablation zone and resulted in a uniform lesion with a size defined by the span of the electrode array. This method is good in the sense that it can generate a bigger lesion on the surface of a targeted area. However, it does not provide any means for controlling the depth of ablation; and the RF electrical current tends to concentrate in the vicinity of the needles. Therefore, this device cannot be used to achieve desirable three-dimensional large lesions consistently.

U.S. Pat. No. 6,514,252 disclosed a device for ablating tissue using two optional arrays of tissue penetration elements (needles) on a pair of actuable jaws using bipolar RF energy. This device extended the electrodes from the forceps to the tip of the needles. However, the application of this device is not really suitable for tumors or other type of tissues due to the fact that it is attached to a jaw mechanism.

For all the reasons mentioned above, there is a need for developing a device, which is capable of producing large and uniform three-dimensional lesions by using bipolar RF energy; and there is a need for developing a method capable of controlling the size and shape of three-dimensional lesions by using bipolar RF energy.

SUMMARY OF THE INVENTION

Accordingly, it is the primary object of the present invention to improve the method for tissue ablation.

It is an object of the present invention to improve the tissue ablation method so that it can be used to ablate tissues with a desirable volume adjacent to a superficial position or at a desirable depth from the surface.

Another object of the present invention is to provide an improved tissue ablation method for achieving the desirable uniformity of lesions created by RF ablation.

It is yet another object of the present invention to improve the ability to configure the lesion created by RF ablation according to the shape and size of diseased tissue.

It is yet another object of the present invention to improve the method of treating tumors and cancerous tissue, and other diseased tissues with benign and malignant pathology such as abnormal endocardiac tissue and prostate gland.

These objects are accomplished by application of plural arrays of segmented needle electrodes, each of which contains a plurality of electrically conductive segments, a plurality of non-conductive joints, and a needle tip. Each of the electrically conductive segments is wired to a RF power source and can be connected to and disconnected from a power source. After the needle electrodes of the device are penetrated into the target tissue to be ablated, the intended volume of ablation can be configured in three dimensions. Thus, the device allows physicians to control ablation boundaries.

In one version of the present invention, each array of segmented needle electrodes contains a series of substantially co-linearly arranged segmented needle electrodes that are spaced at a small distance (a few mm to a few cm). In each array of the segmented needle electrodes, the needle electrodes are spaced close enough so that when all segments of needle electrodes in the same array are connected to the same RF energy source with same polarity, it forms virtually a plate electrode. The array of needle electrodes can be bundled together, partially bundled together, or be individually placed by a user (usually a physician) to allow the user to have control over how to place the needles in the tissue in ablation operations.

Each needle electrode is segmented. Each needle electrode has a plurality of individual segments, and each segment is electrically insulated from other segments and independently wired to a RF power source so that the user can choose to activate any of the segments of a particular needle. Therefore, the user can control the depth of the ablation.

The segmented needle electrodes can also be curved or shaped in a way to target certain tissue at certain anatomic structure to avoid, among other things, bones, major nerves and large blood vessels.

Two arrays of segmented needle electrodes are placed in parallel and adjacent to each other. Two arrays of segmented needle electrodes are then connected to the bipolar RF power source with opposite polarities. Larger lesions can be created by successive adjacent placement of arrays of segmented needle electrodes with alternative polarities.

DETAILED DESCRIPTION OF THE INVENTION

Figure 1:
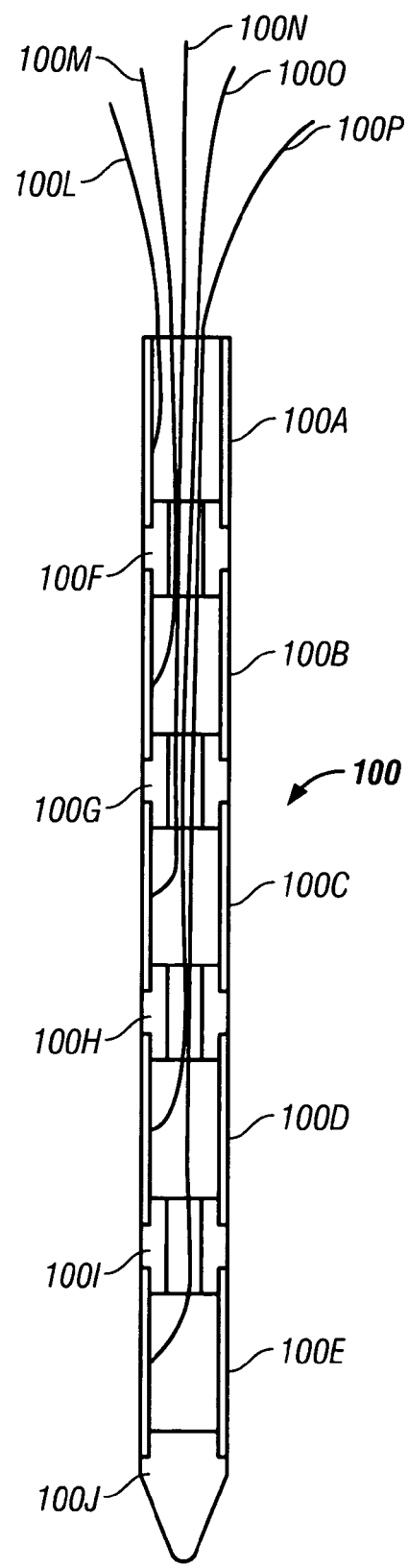
FIG. 1 illustrates the configuration of a single segmented needle electrode.
Figure 2:
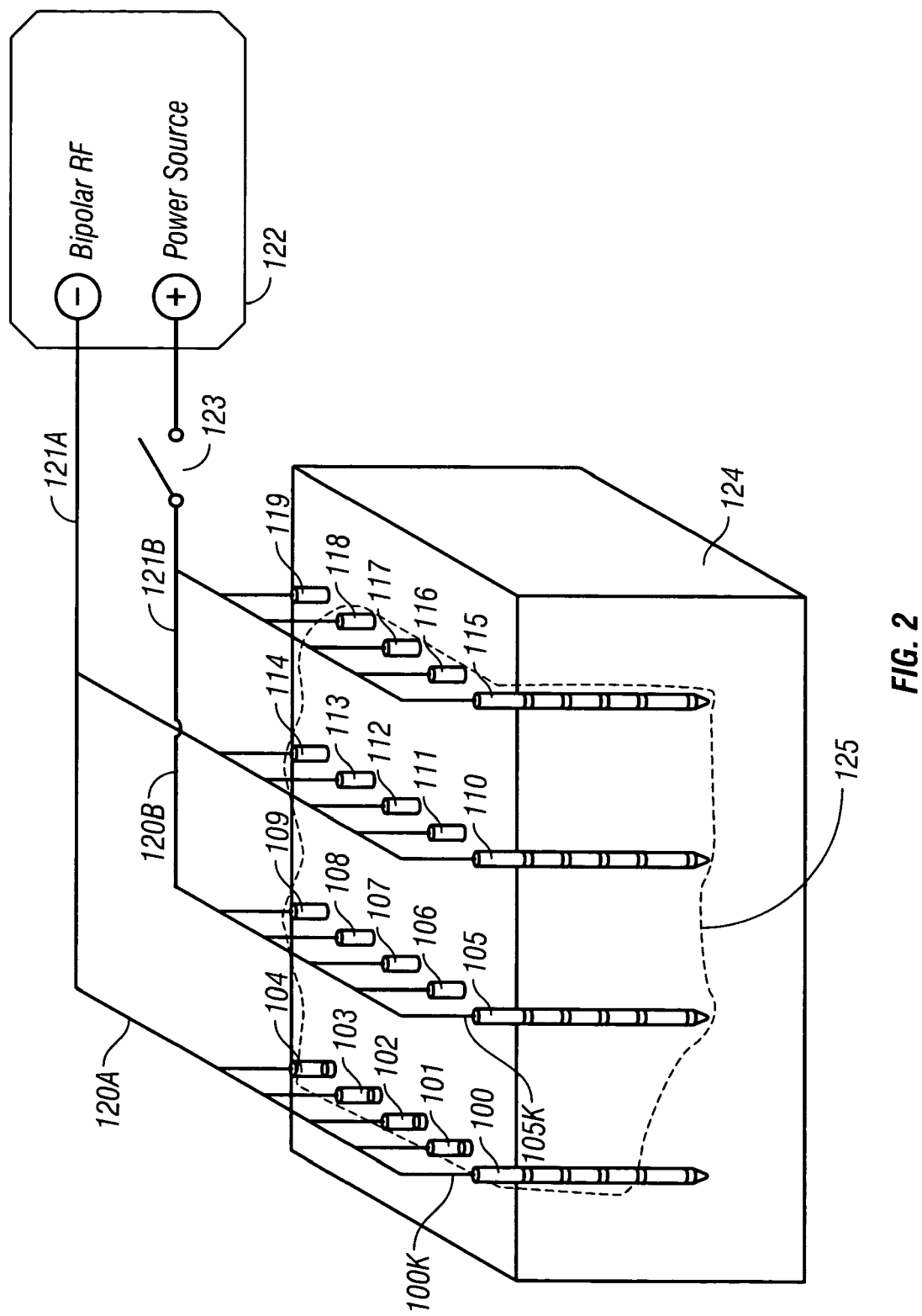
FIG. 2 illustrates schematically the electrode configuration of a multi-array segmented needle electrodes connected to a bipolar RF energy source.

FIGS. 1 and 2 illustrate schematically the configuration and the electrical connection of the improved ablation device. It generally contains a plurality of needle electrodes 100 through 119, arranged in a matrix configuration. The needle electrodes 100 further contains a plurality of electrically conductive metal segments 100A, 100B, 100C, 100D, and 100E, which are jointed by non-conductive tube joints 100F, 100G, 100H, and 100I. A pointing needle tip 100J is assembled at the distal end of the needle electrode 100 to allow for easy penetration into tissues. While the needle tips and metal segments may be made of any of the well known metals such as stainless steel, copper alloys, they may be made of any type of electrically conductive materials.

The metal segments 100A, 100B, 100C, 100D, and 100E are individually wired with a terminal wire bundle look containing five individual wires 100L through 100P, which are individually connected to branch wire bundle 120A, power cable 121A, and a power supply 122 such that each of the metal segments 100A, 100B, 100C, 100D, and 100E can be connected to or disconnected from the power supply 122, which is a bipolar RF power source. All metal segments of other electrodes in the first array are wired to the power supply 122 in a similar way.

The needle electrodes 100 through 104 form an array of electrodes. A second array of the needle electrodes 105 through 109 is formed like the first array. The metal segments of the needle electrode 105 in the second array is wired through a terminal wire bundle 105K, branch wire bundle 120B, and power cable 121B to the power supply 122 through a switch 123. All other segments are wired in the same way. All metal segments of the needle electrodes 105 through 109 in the second array are connected to the power supply 122 on the pole opposite to which the first array of the needle electrodes 100 through 104 are connected. The array of the needle electrodes 100 through 104 may be arranged in a straight or slightly curved line, which is substantially parallel to its neighbor array comprising the needle electrodes 110 through 114.

The third and forth arrays of the needle electrodes 110 through 119 are formed in the same way except that the two arrays are connected to the power supply 122 in opposite polarity. The needle electrodes in the odd arrays are connected to one pole of the power supply 122 and the needle electrodes in the even arrays are connected to the other pole.

The switch 123 may be used to turn on or off the power supply 122. The switch may be installed in any of the two power cables 121A and 121B (or be integrated into the RF power source) and may be controlled by the person who performs the ablation or by temperature or impedance readings feedback from the tissue to be ablated.

In a typical ablation operation (FIG. 2), all the needle electrodes 100 through 119 are penetrated into a targeted tissue 124 such that desired ablation volume 125 (e.g. the tissue to be ablated) is surrounded by the needle electrodes 100 through 119. In this illustration, the fifth metal segment 100E at the distal end of the needle electrode 100 is not connected to the power supply 122 since that segment is outside the boundary of the ablation volume 125. For the purpose of illustration, the needle electrode 119 is not connected to the power supply 122 since it is outside the boundary of the ablation volume 125.

The second array is placed in parallel to the first array with a small distance apart, preferably a few millimeters to a couple of centimeters apart. The distance between two neighbor arrays of the needle electrodes is preferably to be small enough (a few millimeters to a couple of centimeters) to enable this array of the needle electrodes to be a virtual plate electrode. In other words, when electrical power is applied to all the needle electrodes, the electrical potential of the tissues at the middle point between two adjacent needle electrodes of the same array is substantially close to the electrical potential on the surface of those two needle electrodes. Preferably, the distance between the two arrays is close to and somewhat longer than the distance of the two adjacent needles electrodes in the same array to achieve the effect of virtual plate electrodes.

Figure 3:
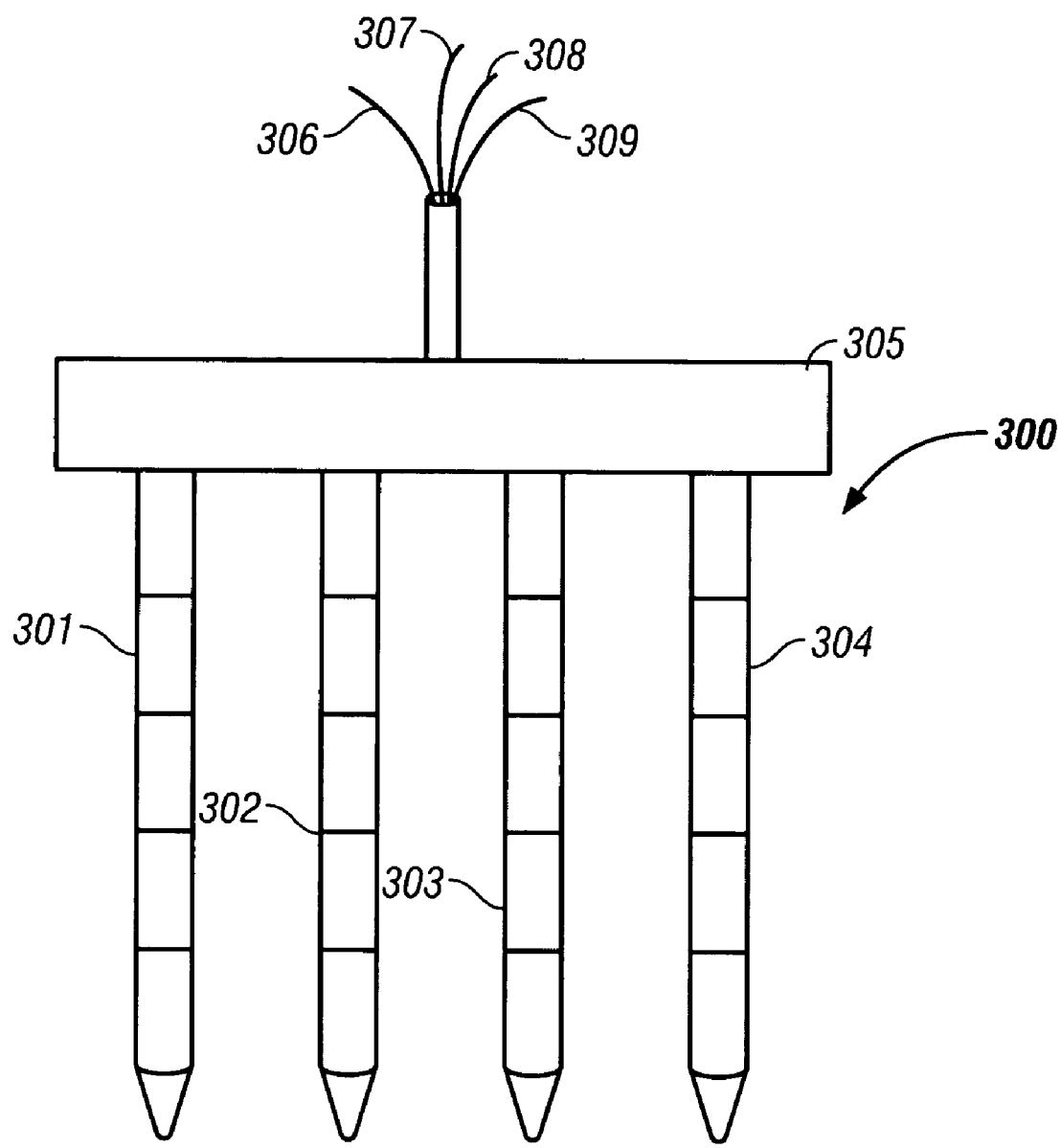
FIG. 3 illustrates schematically an array of segmented needle electrodes bundle.

FIG. 3 illustrates schematically a needle electrode bundle 300 comprising four needle electrodes 301, 302, 303, and 304 assembled together through a non-conductive fixture 305. Each of the wire bundles 306, 307, 308, and 309 is assigned to each of the needle electrodes 301, 302, 303, and 304, respectively; and each of the wire bundles contains a group of individual wires, each being connected to one segment of each of the needle electrodes 301, 302, 303, and 304. A bundled array of the needle electrodes might offer convenience of application, improve the accuracy of ablation, and reduce the time needed to place needles into targeted tissues for certain applications. The needle tip of any needle electrode can be of a shape other than a sharp tip. It can be a blunt tip. By way of example, the tips of the needle electrodes 301 and 302 can join together to form a U-shaped electrode, and the tips of the needle electrodes 303 and 304 can join together to form another U-shaped electrodes. However, they still belong to the same electrode array. This type of configuration may be useful in special cases where tubular tissue structure is to be ablated.

Figure 4:
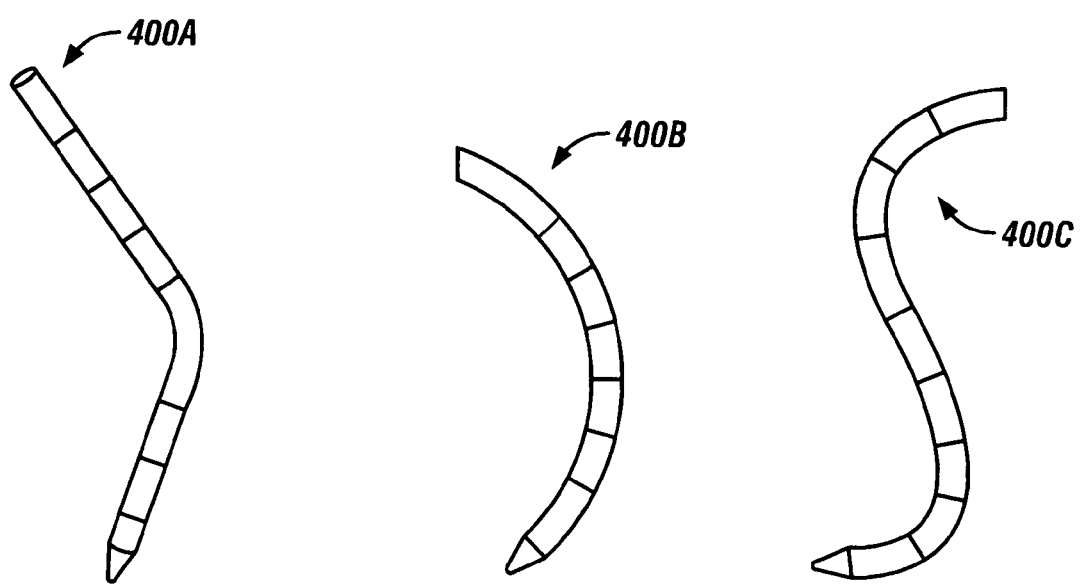
FIG. 4 shows three examples of curved segmented needle electrodes.

FIG. 4 shows three examples of curved needle electrodes 400A, 400B, and 400C. The needle electrode 400A is shaped substantially as a bent line. The needle electrode 400B is curved substantially as a segment of a circle. The needle electrode 400C is shaped substantially as "S" curve. Other shapes are also possible according to specific applications. Those shaped needle electrodes are useful for ablating tissues at certain anatomic locations to avoid bones, major nerves and large vessels.

Figure 5:
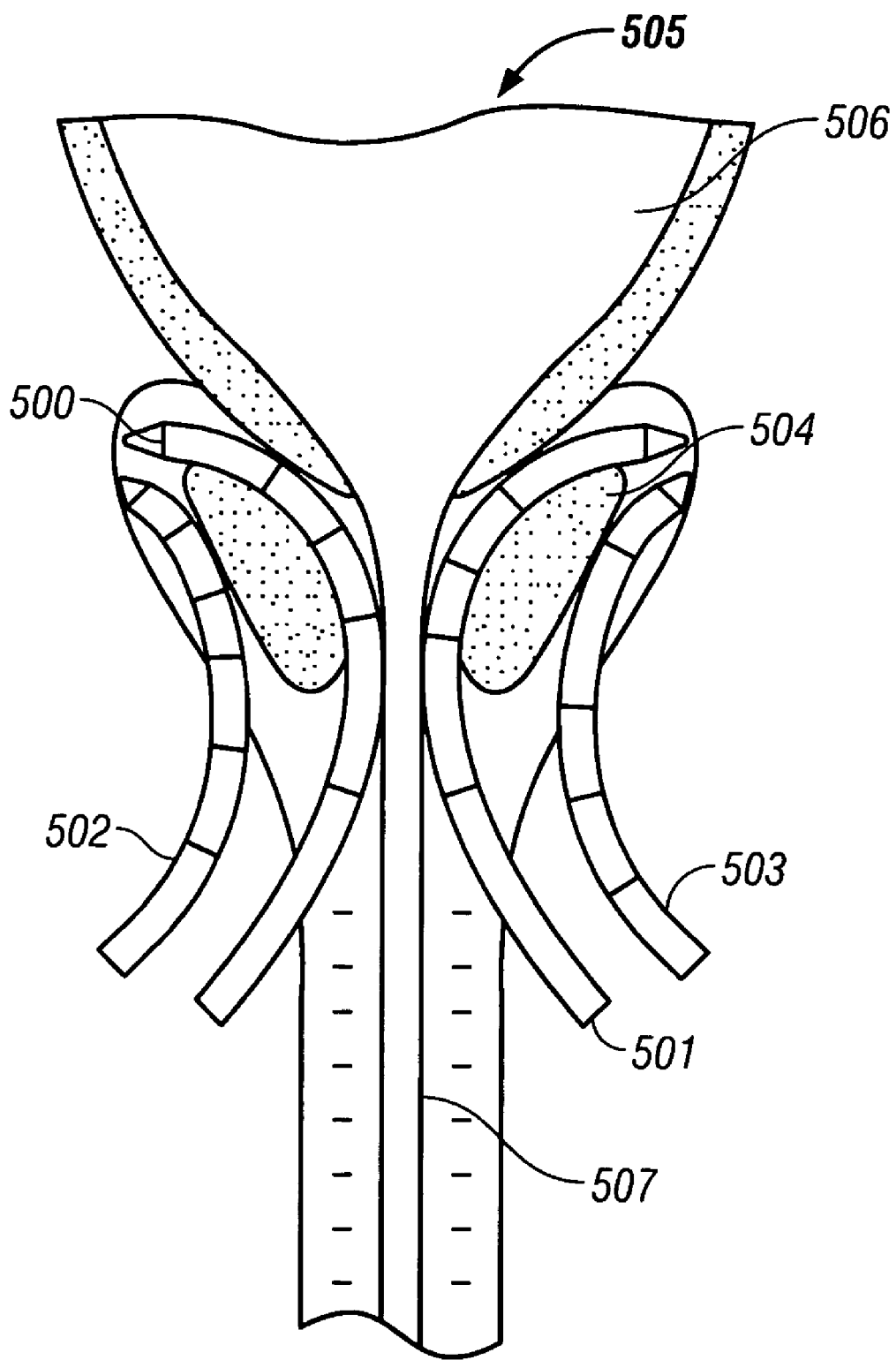
FIG. 5 illustrates an example of using curved segmented needle electrode for ablation of tubular structure.

FIG. 5 illustrates an example of the present invention using curved needle electrodes 500, 501, 502, and 503 for ablation of a tubular structure (generally shown by 505 of FIG. 5). In this case, the tubular structure is a prostate gland 504. The first array of the curved needle electrodes 500 and 501 is placed in the inner tube of the prostate gland 504 in a circular pattern. The second array of the curved needle electrodes 502 and 503 is placed in the outer tube of the prostate gland 504 in a circular pattern. The prostate gland 504 is between the first and second array of the electrodes. The two arrays of the curved needle electrodes are connected to a power supply with opposite polarities (not shown in FIG. 5) with only those segments of electrodes in contact with the prostate gland 504 to be activated. After a delivery of the desired amount of the RF energy, the prostate tissue is ablated. All other surrounding tissues, such as the bladder 506 and the penile 507, would be preserved since most of the RF energy is provided to the tissue between the two arrays of the curved needle electrodes.

In those exemplary embodiments of the present invention, specific components, materials, arrangements, and processes are used to describe the invention. Obvious changes, modifications, and substitutions may be made by those skilled in the art to achieve the same purpose of the invention. The exemplary embodiments are, of course, merely examples and are not intended to limit the scope of the invention. It is intended that the present invention include all other embodiments that are within the scope of the appended claims and their equivalents.

What is claimed is:

1. A system for ablating an intended volume of a target tissue, the system comprising:
    a plurality of needle electrodes,, arranged in arrays with odd and even numbers, with the size being suitable for the target tissue and the intended volume of ablation, each of the needle electrodes having a first end and a second end and having plural electrically conductive segments, at least one nonconductive joint, and a needle tip, wherein any of the two neighbor electrically conductive segments are jointed by one of the at least one nonconductive joint and the needle tip is connected to an electrically conductive segment at the first end of the needle electrode;
    a terminal wire bundle containing plural individual wires at the second end of each needle electrode, each of the individual wires being connected to each of the electrically conductive segments;
    a RF power supply having two poles, one of the poles being connected to the wires of the terminal wire bundles of the needle electrodes in the arrays of odd numbers, and the other pole being connected to the wires of the terminal wire bundles of the needle electrodes in the arrays of even numbers;
    switching means for connecting and disconnecting each of the individual wires; and
    a switch for controlling the power from the power supply to all the electrically conductive segments.

2. The system of claim 1 wherein the number of the electrically conductive segments in any of the needle electrodes is in the range of 2–50.

3. The system of claim 2 wherein the needle electrodes in an array are arranged in a circle line, an S-curve, or any other shape appropriate for the intended volume of ablation.

4. The system of claim 2 wherein the switching means is mechanical contact points in the paths of the individual wires and each of the mechanical contact points can be engaged or disengaged.

5. The system of claim 2 wherein the distance between two adjacent needle electrodes within an array is sufficiently small so that the needle array acts like a virtual plate.

6. The system of claim 2 wherein some of the needle electrodes are not straight.

7. The system of claim 1 wherein the needle electrodes in an array are arranged in a circle line, an S-curve, or any other shape appropriate for the intended volume of ablation.

8. The system of claim 7 wherein the switching means is mechanical contact points in the paths of the individual wires and each of the mechanical contact points can be engaged or disengaged.

9. The system of claim 7 wherein the distance between two neighbor needle electrodes within an array is sufficiently small so that the needle array acts like a virtual plate.

10. The system of claim 7 wherein some of the needle electrodes are not straight.

11. The system of claim 1 wherein the switching means is mechanical contact points in the paths of the individual wires and each of the mechanical contact points can be engaged or disengaged.

12. The system of claim 11 wherein the distance between two neighbor needle electrodes within an array is sufficiently small so that the needle array acts like a virtual plate.

13. The system of claim 11 wherein some of the needle electrodes are not straight.

14. The system of claim 1 wherein the distance between two neighboring needle electrodes within an array is sufficiently small so that the needle array acts like a virtual plate.

15. The system of claim 1 wherein some of the needle electrodes are not straight.

16. A needle electrode assembly for use in an ablation system for ablating an intended volume of a target tissue, the needle electrode comprising:
    a plurality of needle electrodes with length appropriate for tissue ablation wherein each of the needle electrodes comprises plural electrically conductive segments and a needle tip, any of the two neighbor electrically conductive segments are jointed by a nonconductive tube joint, and the needle tip is connected to the neighbor electrically conductive segment;
    a fixture for holding the needle electrodes; and
    a terminal wire bundle containing plural individual wires, each of the individual wires being connected to one of the electrically conductive segments.

17. The needle electrode assembly of claim 16 wherein the number of the electrically conductive segments is in the range of 2–50.

18. The needle electrode assembly of claim 17 wherein the needle electrodes are arranged in a circle line, an S-curve, or any other shape appropriate for the intended volume of ablation.

19. The needle electrode assembly of claim 16 further comprising switching means for connecting and disconnecting each of the individual wires.

20. The needle electrode assembly of claim 16 wherein the needle electrodes are arranged in a circle line, an S-curve, or any other shape appropriate for the intended volume of ablation.

21. The needle electrode assembly of claim 19 wherein the switching means is mechanical contact points in the paths of the individual wires, and each of the mechanical contact points can be engaged or disengaged.

22. The needle electrode assembly of claim 19 wherein the switching means is switches that can be turned on or off by a controlling device.

23. A method of ablating an intended ablation volume of a target tissue using an ablation system, the ablation system comprising a plurality of needle electrodes in arrays of odd numbers and even numbers, a power supply with two connection poles, and a main switch, each of the needle electrodes comprising plural electrically conductive segments, plural individual wires, at least one nonconductive joint, and a needle tip, any of the two neighbor electrically conductive segments being jointed by one of the at least one nonconductive joint, the needle tip being connected to an electrically conductive segment at a first end of the needle electrode, each of the electrically conductive segments in each of the needle electrodes being connected to one of the individual wires, the wires from each of the needle electrodes forming a terminal wire buddle at a second end of the needle electrode, each of the individual wires having switching means, the method comprising the steps of:

inserting the plurality of needle electrodes into the target tissue in a proper way so that at least some of the intended volume of the target tissue being substantially between two of the arrays of the needle electrodes;

connecting all the individual wires of the terminal wire bundles of the needle electrodes in the arrays of odd numbers to one of the poles of the power supply;

connecting all the individual wires of the terminal wire bundles of the needle electrodes in the arrays of even numbers to the other pole of the power supply;

engaging the switching means of each of the wires which are connected to the electrically conductive segments that are within the intended ablation volume;

disengaging the switching means of each of the wires that are connected to the electrically conductive segments that are outside of the intended ablation volume;

applying power to all the electrically conductive segments that are connected to the power supply by turning on the main switch of the power supply;

ablating the target tissue until a sufficient amount of energy is delivered; and removing the needle electrodes from the tissue.

24. The method of claim 23 wherein the number of the electrically conductive segments is in the range of 2–50.

25. The method of claim 23 wherein the needle electrodes are arranged in a circle line, an S-curve, or any other shape appropriate for the intended volume of ablation.

* * * * *